(12) United States Patent
Leger et al.

(10) Patent No.: US 8,395,003 B2
(45) Date of Patent: *Mar. 12, 2013

(54) METAL NANOPARTICLE-BASED CATALYTIC COMPOSITION THAT CONTAINS A NITROGEN-CONTAINING LIGAND IN AN IONIC LIQUID, PROCESS FOR PREPARATION, PROCESS FOR HYDROGENATION OF AN OLEFINIC FEEDSTOCK

(75) Inventors: Bastien Leger, Charleville-Mezieres (FR); Alain Roucoux, Thorigne-Fouillard (FR); Helene Olivier-Bourbigou, Saint Genis-Laval (FR)

(73) Assignee: IFP Energies Nouvelles, Rueil Malmaison Cedex (FR)

( * ) Notice: Subject to any disclaimer, the term of this patent is extended or adjusted under 35 U.S.C. 154(b) by 422 days.

This patent is subject to a terminal disclaimer.

(21) Appl. No.: 12/597,341

(22) PCT Filed: Apr. 14, 2008

(86) PCT No.: PCT/FR2008/000524
§ 371 (c)(1),
(2), (4) Date: Mar. 25, 2010

(87) PCT Pub. No.: WO2008/145836
PCT Pub. Date: Dec. 4, 2008

(65) Prior Publication Data
US 2010/0191027 A1    Jul. 29, 2010

(30) Foreign Application Priority Data
Apr. 26, 2007  (FR) ..................... 07 03114

(51) Int. Cl.
*C07C 5/02* (2006.01)
*B01J 31/28* (2006.01)
(52) U.S. Cl. ........ 585/277; 585/275; 585/276; 502/150; 502/162; 502/164; 502/166; 502/167; 502/173; 977/773; 977/778; 977/786
(58) Field of Classification Search .............. 502/150, 502/162, 164, 166, 167, 173; 585/275, 276, 585/277; 252/363.5; 75/255; 977/773, 775, 977/777, 778, 779, 786
See application file for complete search history.

(56) References Cited

U.S. PATENT DOCUMENTS

| | | | | |
|---|---|---|---|---|
| 5,973,218 A * | 10/1999 | Ashida et al. | .................. | 585/273 |
| 6,040,263 A * | 3/2000 | Mussmann et al. | ............ | 502/164 |
| 6,114,272 A * | 9/2000 | Bahrmann | .................... | 502/164 |
| 6,455,746 B1 * | 9/2002 | Dubois et al. | .................. | 585/258 |
| 2006/0129010 A1 * | 6/2006 | Hillion et al. | .................. | 585/527 |

FOREIGN PATENT DOCUMENTS

| | | |
|---|---|---|
| EP | 1 698 686 A | 9/2006 |
| WO | WO 2005/019185 A | 3/2005 |

OTHER PUBLICATIONS

Roucoux, et al., "Reduced Transition Metal Colloids: A Novel Family of Reusable Catalysts?" in Chem. Rev., 2002, 102, 3757-3778 available on-line Sep. 10, 2002.*

Dyson, et al., Metal Catalyzed Reactions in Ionic Liquids, Springer, 2005, available on-line Jan. 24, 2006.*

House, "Ammonia and N-Donor Ligands" in Encyclopedia of Inorganic Chemistry, John Wiley & Sons, 2006, available on-line Mar. 15, 2006.*

Paul, et al., "Synthesis and Characterization of Rhodium Complexes Containing 2,4,6-Tris(2-pyridyl)-1,3,5-triazine and Its Metal-Promoted Hydrolytic Products" in Inorg. Chem., 1998, 37, 5733-5742.*

Huang, et al., "Hydrogenation of Olefins Using Ligand-Stabilized Palladium Nanoparticles in an Ionic Liquid" in Chem. Commun., 2003,1654-1655, available on-line Jun. 6, 2003.*

"International Search Report," Application No. PCT/FR2008/000524, Completed Dec. 4, 2008, Date of Mailing Dec. 12, 2008, 3 pages.

Mu Xin-Dong, "A general method for preparation of PVP-stabilized noble metal nanoparticles in room temperature ionic liquids," Catal Lett; Cataliysts Letters September 2004, vol. 97, No. 3-4, XP002466340.

(Continued)

*Primary Examiner* — In Suk Bullock
*Assistant Examiner* — Bradley Etherton
(74) *Attorney, Agent, or Firm* — Millen, White, Zelano & Branigan, P.C.

(57) ABSTRACT

The object of this invention is a suspension of metal nanoparticles with a mean size of between 1 and 20 nanometers, in at least one non-aqueous ionic liquid, whereby said suspension also contains at least one nitrogen-containing ligand, in which said metal nanoparticles comprise at least one transition metal in the zero valence state that is selected from among rhodium, ruthenium, iridium, nickel, and platinum by themselves or in a mixture and in which said nitrogen-containing ligand is selected from the group that is formed by the linear compounds that comprise at least one nitrogen atom, whereby the non-aromatic cyclic compounds comprise at least one nitrogen atom, the non-condensed aromatic compounds comprise at least one nitrogen atom, the condensed aromatic compounds comprise at least one group of two aromatic cycles that are condensed two by two, and at least one nitrogen atom, whereby the condensed aromatic compounds comprise at least 3 aromatic cycles and 1 nitrogen atom, and whereby the condensed aromatic compounds comprise at least 3 aromatic cycles and at least 2 nitrogen atoms that are located in the same aromatic cycle.

29 Claims, No Drawings

OTHER PUBLICATIONS

Fonseca G S et al: "The use of imidazlium ionic liquids for the formation and stabilization of Ir DEG and for the hydrogenation of arenas," Chemistry—A European Journal, VCH Publishers, US, vol. 9, 2003, pp. 3263-3269, XP002462143, ISSN: 0947-6539.

Jun Huang et al: "Hydrogenation of olefins using ligand-stabilized nanoparticles in an ionic liquid",Chemical Communications-Chemcom, Royal Society of Chemistry, GB, 2003, pp. 1654-1655, XP002462142, ISSN:1359-7345.

Yinghuai Zhu et al: "Ruthenium(0) nanoparticle-catalyzed isotope exchange between $^{10}B$ and $^{11}B$ nuclei in decaborane(14)," J.Am.Chem.Soc.: Journal of the American Chemical Society May 23, 2007, vol. 129, No. 20, pp. 6507-6512, XP002466341.

Deng et al: "Biphasic asymmetric hydroformylation and hydrogenation by water-soluble rhodium and ruthenium complexes of sulfonated ®-2,2' bis(diphenylphosphino)-1,'-binap hthyl in ionic liquids" Journal of Molecular Catalysts. A, Chemical,Elsevier,Amsterdam, NL, vol. 270, No. 1-2 May 7, 2007, pp. 76-82, XP022044424 ISSN:1381-1169.

* cited by examiner

METAL NANOPARTICLE-BASED CATALYTIC COMPOSITION THAT CONTAINS A NITROGEN-CONTAINING LIGAND IN AN IONIC LIQUID, PROCESS FOR PREPARATION, PROCESS FOR HYDROGENATION OF AN OLEFINIC FEEDSTOCK

SCOPE OF THE INVENTION

This invention describes a suspension of metal nanoparticles with a mean size of between 1 and 20 nanometers, in at least one non-aqueous ionic liquid, whereby said suspension also contains at least one nitrogen-containing ligand, in which said metal nanoparticles comprise at least one transition metal in the zero valence state that is selected from among rhodium, ruthenium, iridium, nickel, and platinum by themselves or in a mixture and in which said nitrogen-containing ligand is selected from the group that is formed by the linear compounds that comprise at least one nitrogen atom, whereby the non-aromatic cyclic compounds comprise at least one nitrogen atom, the non-condensed aromatic compounds comprise at least one nitrogen atom, the condensed aromatic compounds comprise at least one group of two aromatic cycles that are condensed two by two, and at least one nitrogen atom, whereby the condensed aromatic compounds comprise at least 3 aromatic cycles and 1 nitrogen atom, and whereby the condensed aromatic compounds comprise at least 3 aromatic cycles and at least 2 nitrogen atoms that are located in the same aromatic cycle.

PRIOR ART

The use of nanoparticles of transition metals for catalyzing the hydrogenation of unsaturated compounds is currently experiencing a significant resurgence as it is described in the literature. These catalysts that generally comprise a transition metal in the zero-valence state are very advantageous due to their unique properties, such as, for example, their large specific surface area that imparts to them excellent reactivity and good selectivity even under mild reaction conditions. One of the primary characteristics of these particles is their small size that is generally between 1 and 3 nm.

Several methods for synthesis of nanoparticles are described: electrochemical, sonochemical, condensation of metal vapors, . . . but the most commonly used and the most simple implements a chemical reduction of transition metal salts [see: A. Roucoux, J. Schulz, H. Patin, *Chem. Rev.* 2002, 102, 3757]. The size of the particles may depend, however, on the reduction conditions (nature of the reducing agents, concentration, solvent, . . . ). Different types of reducing agents have been used, such as hydrides or metallic salts, molecular hydrogen, carbon monoxide, or else organic compounds that can be oxidized, such as reducing alcohols. The reduction can be done starting from the corresponding metallic salt or else by reaction of an organometallic precursor with molecular hydrogen by ligand displacement.

The nanoparticles of the transition metals are naturally not very stable and have a strong tendency to become agglomerated, thus losing their nanoscopic nature. This aggregation usually brings about the loss of properties linked to their colloidal state and is generally reflected in catalysis by a loss of activity and reproducibility problems. The stabilization of the metal nanoparticles and therefore the preservation of their finely divided nature is a basic stage during their synthesis.

Several types of stabilization have been taken into consideration:

(i) Electrostatic stabilization. This is a Coulomb repulsion that is generated by the use of ionic compounds (chloride, carboxylates or polyoxoanions) that are adsorbed on the surface of the nanoparticles and that generate a double electric layer because of the presence of the counter-ion, (ii) The steric stabilization that is based on the use of ligands or macromolecules such as polymers or oligomers, (iii) The combination of these last two stabilization methods, namely the electrosteric stabilization (for example with the use of ionic surfactants or ligands).

The catalytic activity and the selectivity of these nanoparticles in solution depends not only on the relative abundance of the different active sites but also on the concentration and the type of stabilizers that are present in the medium.

However, if the nanoparticles of the transition metals have numerous advantages in catalysis, these catalysts can also generate certain drawbacks:

In general, they are not very stable thermally and can rapidly agglomerate,

The separation of the soluble catalyst from the products of the reaction can pose a problem.

The combination of a ligand and an ionic liquid has been sparingly described for the synthesis and the stabilization of nanoparticles. However, the presence of the ligand can have a double advantage: "to solubilize" the active radicals (nanoparticles) in the non-aqueous ionic liquids and to modulate their reactivity (selectivity and activity). Nanoparticles that are stable in solution are then obtained. The combination of a ligand, a metal and an ionic liquid can provide a noteworthy synergetic effect that makes it possible to enhance the catalytic activity of these systems and to improve their stability (service life). Furthermore, their separation from the products of the reaction and their recycling can be done by simple decanting in a two-phase liquid-liquid catalysis process and/ or by liquid-liquid extraction.

The studies concern the combination of a metal compound, a nitrogen-containing ligand, and a non-aqueous ionic liquid as a catalytic composition, and it has now been found that the use of such a combination made it possible to avoid the drawbacks cited above, while improving the catalytic activity and the stability of the catalytic system and by making possible a very simple separation of the reaction products as well as the recycling of said catalytic composition.

OBJECT OF THE INVENTION

This invention has as its object a suspension of metal nanoparticles with a mean size of between 1 and 20 nanometers, in at least one non-aqueous ionic liquid, whereby said suspension also contains at least one nitrogen-containing ligand, in which said metal nanoparticles comprise at least one transition metal in the zero valence state that is selected from among rhodium, ruthenium, iridium, nickel, and platinum by themselves or in a mixture and in which said nitrogen-containing ligand is selected from the group that is formed by the linear compounds that comprise at least one nitrogen atom, whereby the non-aromatic cyclic compounds comprise at least one nitrogen atom, the non-condensed aromatic compounds comprise at least one nitrogen atom, the condensed aromatic compounds comprise at least one group of two aromatic cycles that are condensed two by two, and at least one nitrogen atom, whereby the condensed aromatic compounds comprise at least 3 aromatic cycles and 1 nitrogen atom, and whereby the condensed aromatic compounds comprise at least 3 aromatic cycles and at least 2 nitrogen atoms that are located in the same aromatic cycle.

This invention also has as its object a process for preparation of said suspension of metal nanoparticles in at least one non-aqueous ionic liquid.

This invention also has as its object a process for hydrogenation of a non-aromatic unsaturated feedstock that as catalytic composition uses said suspension of metal nanoparticles in at least one non-aqueous ionic liquid.

DETAILED DESCRIPTION OF THE INVENTION

The invention relates to a suspension of metal nanoparticles in at least one non-aqueous ionic liquid, a process for preparation of said suspension of metal nanoparticles, and a process for hydrogenation of a non-aromatic unsaturated feedstock that as catalytic composition uses said suspension of metal nanoparticles in said non-aqueous ionic liquid.

Nanoparticles are defined as particles whose size can vary from several angstroms to several tens of nanometers.

The size of the nanoparticles is determined by all of the methods that are known to one skilled in the art.

Transmission electron microscopy (TEM) makes it possible, for example, to characterize the metal nanoparticles and to obtain direct visual information on the size, the shape, the dispersion, the structure and the morphology of the nanoparticles.

According to the invention, the mean size of the nanoparticles is between 1 and 20 nanometers. Preferably, the mean size of the nanoparticles is between 1 and 10 nanometers. The mean size of the particles according to the invention is determined from the measurement of a lot of 400 particles per sample using counting software based on shape recognition.
Process for the Preparation of the Suspension of Metal Nanoparticles in a Non-Aqueous Ionic Liquid.

The suspension of metal nanoparticles in at least one ionic liquid according to the invention is obtained by chemical reaction, by a simple bringing into contact of a metal precursor of transition metals selected from among rhodium, ruthenium, iridium, nickel, and platinum by themselves or in a mixture, a reducing agent, at least one ionic liquid and at least one nitrogen-containing ligand, defined below, optionally in the presence of an organic solvent, whereby the contact is followed by stirring and the addition of different components can be done in any order.

Preferably, the addition of the nitrogen-containing ligand can be done in a second stage that follows a first stage for bringing into contact the metal precursor, the reducing agent, and at least one ionic liquid. In this case, the addition of the ligand is done after the metal precursor reacts with the reducing agent in the presence of the ionic liquid and optionally the organic solvent.

The metal precursors are preferably metallic salts of transition metals that are selected from among halides (such as, for example, chlorides, bromides, or else iodides), acetates, sulfates, carboxylates, phenates and acetylacetonates.

The metal precursors preferably can also be organometallic complexes or oxides.

The reducing agent is preferably selected from among metals and metallic salts, alkaline hydrides, and organic compounds that can be oxidized, whereby said organic compounds that can be oxidized can also be used as solvents. The reduction can also be carried out by molecular hydrogen or carbon monoxide.

More preferably, the reducing agent is a metal that is selected from among zinc, aluminum and lithium.

The reducing agent can also be a metallic salt such as, for example, sodium citrate.

The reducing agent can also be a hydride that is selected from among sodium borohydride, potassium borohydride, or lithium aluminum tetrahydride ($LiAlH_4$).

As a reducing agent, it is also possible to use an organic compound that is preferably selected from among ascorbic acid or hydrazine, or else an organic solvent that can be oxidized, selected from among methanol, ethanol, 2-propanol, ethylene glycol, and propylene glycol.

The non-aqueous ionic liquids and the nitrogen-containing ligands according to the invention are defined later in the description.

According to a preferred embodiment, the procedure is performed in the presence of an organic solvent that is selected from among aliphatic or aromatic hydrocarbon compounds, aromatic hydrocarbons, halogenated hydrocarbon compounds, ethers and alcohols.

When one organic solvent is used, it can be eliminated at the end of the reaction of the suspension of metal nanoparticles in the ionic liquid by all of the methods that are known to one skilled in the art and preferably by evaporation under reduced pressure.

Said suspension of metal nanoparticles in the ionic liquid that is thus obtained is then used just as is after evaporation of the solvent in the process for hydrogenation of the aromatic compounds according to the invention.

Said suspension of metal nanoparticles in the ionic liquid is prepared under the following operating conditions:

The temperature of the reaction is between −20° C. and 200° C. and preferably between −10° C. and 100° C.

The pressure is between 1 and 80 bar and preferably between 1 and 50 bar.

The molar ratio between the reducing agent and the metal precursor is between 1 and 50 and preferably between 1 and 5.

It should be noted that in the case of organic solvents being used as reducing agents, the quantity of solvent and therefore of reducing agent is not limited.

The molar ratio between the ligand and the metallic precursor metal is between 0.001 and 100, preferably between 0.01 and 10, more preferably the molar ratio is greater than 0.05 and strictly less than 1, even more preferably between 0.05 and 0.8, and even more preferably between 0.05 and 0.6.

The metal concentration in the ionic liquid is between $1.9 \times 10^{-5}$ and 19 mol $L^{-1}$, and preferably between $1.9 \times 10^{-5}$ and 1.9 mol $L^{-1}$.

The suspension of metal nanoparticles in the non-aqueous ionic liquid that is prepared as disclosed above will now be described more specifically within the framework of its use as a catalytic composition for a process for hydrogenation of non-aromatic unsaturated feedstocks according to the invention. Said catalytic composition comprises three characteristic elements: the metal, the nitrogen-containing ligand, and the non-aqueous ionic liquid.
The Metal According to the invention, the transition metal is selected from the group that is formed by rhodium, ruthenium, iridium, nickel, and platinum, by themselves or in a mixture.

According to one preferred embodiment, the metal is selected from among rhodium, ruthenium and iridium, by themselves or in a mixture.

According to an even more preferred embodiment, the metal is rhodium.

According to another even more preferred embodiment, the metal is ruthenium.

Said catalytic composition also comprises at least one nitrogen-containing ligand.

The Ligand

According to the invention, the nitrogen-containing ligand [is] selected from the group that is formed by the linear compounds that comprise at least one nitrogen atom, non-aromatic cyclic compounds that comprise at least one nitrogen atom, non-condensed aromatic compounds that comprise at least one nitrogen atom, condensed aromatic compounds that comprise at least one group of two aromatic cycles that are condensed two by two and at least one nitrogen atom, whereby the condensed aromatic compounds comprise at least 3 aromatic cycles and 1 nitrogen atom, and the condensed aromatic compounds comprise at least 3 aromatic cycles and at least 2 nitrogen atoms that are located on the same aromatic cycle.

A condensed aromatic compound is defined as any aromatic compound that comprises at least two aromatic cycles that are attached by a carbon-carbon bond of the cycle.

According to a first preferred embodiment, the nitrogen-containing ligand is selected from among the linear compounds that comprise preferably 1 to 20 nitrogen atoms, more preferably 1 to 10 nitrogen atoms, and even more preferably 1 to 7 nitrogen atoms.

In the embodiment where the nitrogen-containing ligand is selected from among the linear compounds, the nitrogen-containing ligand is preferably selected from among the families of alkylamines, diamines, polyamines and polyethyleneimines, whose general formulas are shown below:

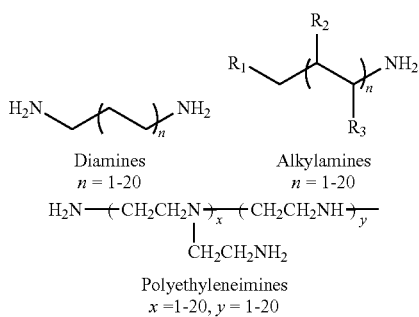

Diamines
$n = 1\text{-}20$

Alkylamines
$n = 1\text{-}20$

Polyethyleneimines
$x = 1\text{-}20, y = 1\text{-}20$

In the embodiment where the nitrogen-containing ligand is selected from among the non-aromatic cyclic compounds, the nitrogen-containing ligand is preferably selected from among the compounds that comprise preferably 1 to 20 nitrogen atoms, more preferably 1 to 10 nitrogen atoms, and even more preferably 1 to 7 nitrogen atoms.

More preferably, the nitrogen-containing ligand is selected from among the non-aromatic cyclic compounds from the families of bipiperidines and substituted bipiperidines, polyazacycloalkanes, oxazolidines and substituted oxazolidines, and oxazolines and substituted oxazolines, whose general formulas are shown below:

The substituted bipiperidines, whereby the amine group —NH can occupy the positions 2-2',3-3' and 4-4'.

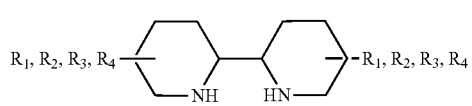

The polyazacycloalkanes with n=[1; 100], p=[1; 20], m=[1; 10], x=[1; 100], and y=[1; 100]

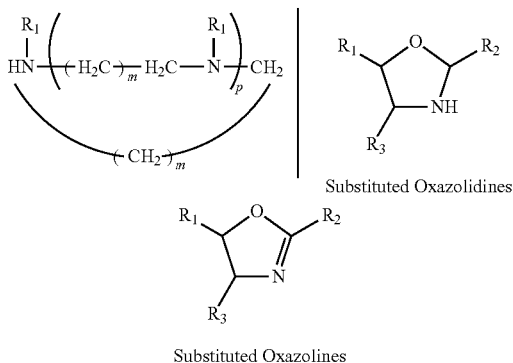

Substituted Oxazolidines

Substituted Oxazolines

In the embodiment where the nitrogen-containing ligand is selected from among the non-condensed aromatic compounds, the nitrogen-containing ligand is preferably selected from among the compounds that comprise preferably 1 to 20 nitrogen atoms, more preferably 1 to 10 nitrogen atoms, and even more preferably 1 to 7 nitrogen atoms.

More preferably, the nitrogen-containing ligand is selected from among the non-condensed aromatic compounds from the families of pyridines and substituted pyridines, bipyridines and substituted bipyridines, bis(2-pyridyl)alkanes, bis(3-pyridyl)alkanes, bis(4-pyridyl)alkanes and bis(2-pyridinyl)alkanes, and substituted bis(2-pyridyl)alkanes, substituted bis(3-pyridyl)alkanes, substituted bis(4-pyridyl)alkanes and substituted bis(2-pyridinyl)alkanes, pyrazines and substituted pyrazines, and triazines and substituted triazines, whose general formulas are shown below:

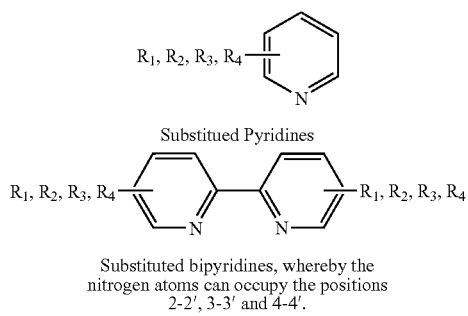

Substitued Pyridines

Substituted bipyridines, whereby the nitrogen atoms can occupy the positions 2-2', 3-3' and 4-4'.

Substituted bis(2-pyridyl)alkanes, whereby the nitrogen atoms can occupy the positions 2-2',3-3', and 4-4', and n is between 1 and 20.

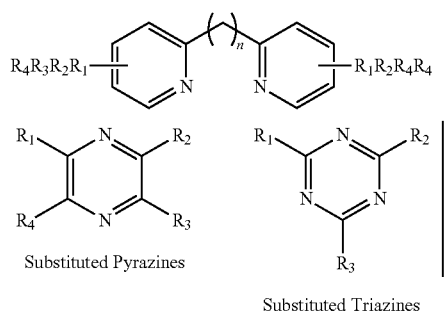

Substituted Pyrazines

Substituted Triazines

When the nitrogen-containing ligand is selected from among the non-condensed aromatic compounds from the family of substituted pyrazines, preferably, the nitrogen-containing ligand is tetra-2-pyridinyl-pyrazine or TPPZ or the bis-pyridyl-pyrazine of the general formulas that are shown below:

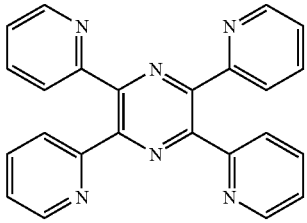

Tetra-2-pyridinyl-pyrazine or TPPZ

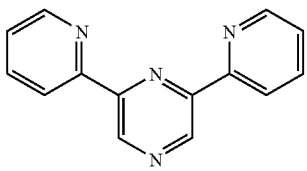

bis-Pyridyl-pyrazine

More preferably, the nitrogen-containing ligand is tetra-2-pyridinyl-pyrazine or TPPZ.

When the nitrogen-containing ligand is selected from among the non-condensed aromatic compounds from the family of substituted triazines, preferably, the nitrogen-containing ligand is 2,4,6-tris-(2-pyridyl)-s-triazine or TPST of the general formula that is shown below:

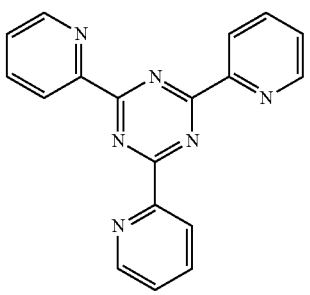

In the embodiment where the nitrogen-containing ligand is selected from among the condensed aromatic compounds comprising at least one group of 2 aromatic cycles that are condensed two by two, the nitrogen-containing ligand is preferably selected from among the compounds that comprise preferably 1 to 20 nitrogen atoms, more preferably 1 to 10 nitrogen atoms, and even more preferably 1 to 7 nitrogen atoms.

More preferably, the nitrogen-containing ligand is selected from among the condensed aromatic compounds that comprise at least one group of 2 aromatic cycles that are condensed two by two from the families of naphpyridines and substituted naphpyridines, quinolines and substituted quinolines, and isoquinolines and substituted isoquinolines, whose general formulas are shown below.

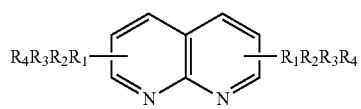

Substituted Naphpyridines

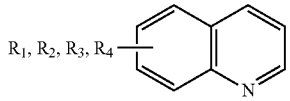

Substituted Quinolines

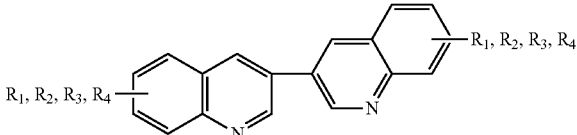

Substituted bis-Quinolines

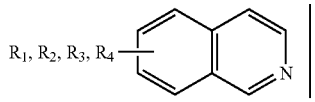

Substituted Isoquinolines

In the embodiment where the nitrogen-containing ligand is selected from among the condensed aromatic compounds that comprise at least 3 aromatic cycles and one nitrogen atom, the nitrogen-containing ligand is preferably selected from among the compounds from the families of the dibenzopyridines and substituted dibenzopyridines and phenanthridines and substituted phenanthridines.

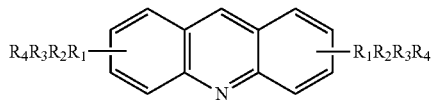

Substituted Dibenzopyridines

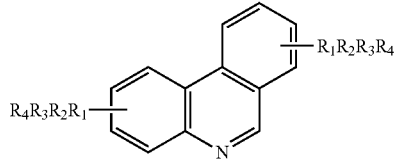

Substituted Phenanthridines

In the embodiment where the nitrogen-containing ligand is selected from among the condensed aromatic compounds that comprise at least 3 aromatic cycles and at least two nitrogen atoms that are located on the same aromatic cycle, the nitrogen-containing ligand is preferably selected from among the compounds from the families of phenazines and substituted phenazines.

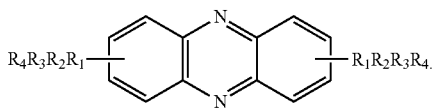

Substituted Phenazines.

In all of the general formulas of the compounds above, the groups R1, R2, R3 and R4 can be identical or different. The groups R1, R2, R3 and R4 are advantageously alkyl radicals, cycloalkyl radicals, aryl radicals or aralkyl radicals, comprising 1 to 10 carbon atoms. They can also comprise a functional group, such as, for example, an amine, a cyclic amine, a nitrogen-containing heterocycle, an ester, an acid, an alcohol, a quaternary ammonium, an imidazolium cation, a pyrrolidinium cation, a pyridinium cation, a quaternary phosphonium, a sulfonium, a sulfonate or a phosphonate.

Said catalytic composition also comprises a non-aqueous ionic liquid.

The Non-Aqueous Ionic Liquids:

The non-aqueous ionic liquids are generally compounds that are represented by the general formula $Q^+A^-$ and are prepared according to preparation methods that are known to one skilled in the art.

The $A^-$ anions are preferably selected from among the following anions: halides, nitrates, sulfates, alkylsulfates, phosphates, alkylphosphates, acetates, haloacetates, tetrafluoroborates, tetrachloroborates, hexafluorophosphates, trifluoro-tris-(pentafluoroethyl)phosphates, hexafluoroantimonates, fluorosulfonates, alkylsulfonates, such as, for example, methylsulfonate; perfluoroalkylsulfonate anions, such as, for example, trifluoromethylsulfonate; bis(perfluoroalkylsulfonyl)amide anions, such as, for example, the bis-trifluoromethylsulfonyl amide of formula $N(CF_3SO_2)_2^-$, the tris-trifluoromethylsulfonyl methylide of formula $C(CF_3SO_2)_3^-$, the bis-trifluoromethylsulfonyl methylide of formula $HC(CF_3SO_2)_3^-$; the arenesulfonate anions, optionally substituted by halogen or haloalkyl groups; the tetraphenylborate anion, and the tetraphenylborate anions whose aromatic cores are substituted; the tetra-(trifluoroacetoxy)-borate anion, the bis-(oxalato)-borate anion, the dicyanamide anion, the tricyanomethylide anion, as well as the chloroaluminate anions or the chlorozincate anions, and the chloroferrate anions.

The $Q^+$ cations are preferably selected from among the group that is formed by phosphoniums, ammoniums, guanidiniums and sulfoniums.

In all of the general formulas that are represented below, the groups $R^1$, $R^2$, $R^3$, $R^4$, $R^5$ and $R^6$ advantageously represent hydrogen (with the exception of the $NH_4^+$ cation for $NR^1R^2R^3R^{4+}$), preferably a single substituent that represents hydrogen, or hydrocarbyl radicals that have 1 to 30 carbon atoms, for example alkyl groups that may or may not be saturated, cycloalkyl or aromatic groups, aryl or aralkyl groups, optionally substituted, comprising 1 to 30 carbon atoms.

The groups $R^1$, $R^2$, $R^3$, $R^4$, $R^5$ and $R^6$ can also represent hydrocarbyl radicals that carry one or more groups that are selected from among the groups —$CO_2R$, —$C(O)R$, —OR, —$C(O)NRR'$, —$C(O)N(R)NR'R''$, —$NRR'$, —SR, —$S(O)R$, —$S(O)_2R$, —$SO_3R$, —CN, —$N(R)P(O)R'R'$, —$PRR'$, —$P(O)RR'$, —$P(OR)(OR')$, —$P(O)(OR)(OR')$, in which the groups R, R' and R", identical or different, each represent hydrogen or hydrocarbyl radicals that have 1 to 30 carbon atoms.

The sulfonium and guanidium cations preferably correspond to one of the general formulas $SR^1R^2R^{3+}$ or $C(NR^1R^2)(NR^3R^4)(NR^5R^6)^+$, where the groups $R^1$, $R^2$, $R^3$, $R^4$, $R^5$ and $R^6$, identical or different, are defined as above.

The $Q^+$ quaternary ammonium and phosphonium cations preferably correspond to one of the general formulas $NR^1R^2R^3R^{4+}$ and $PR^1R^2R^3R^{4+}$, or to one of the general formulas $R^1R^2N=CR^3R^{4+}$ and $R^1R^2P=CR^3R^{4+}$, in which $R^1$, $R^2$, $R^3$, and $R^4$, identical or different, are defined as above.

The $Q^+$ ammonium and phosphonium cations can also be derived from nitrogen-containing and/or phosphorus-containing heterocycles comprising 1, 2 or 3 nitrogen atoms and/or phosphorus atoms, of the general formulas below:

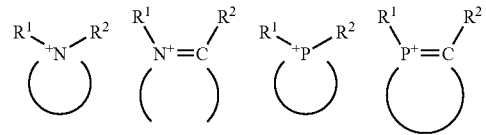

in which the cycles consist of 4 to 10 atoms, preferably 5 to 6 atoms, and $R^1$ and $R^2$, identical or different, are defined as above.

The $Q^+$ quaternary ammonium and phosphonium cations can also correspond to one of the general formulas: $R^1R^{2+}N=CR^3—R^7—R^3C=N^+R^1R^2$ and $R^1R^{2+}P=CR^3—R^7—R^3C=P^+R^1R^2$, in which the groups $R^1$, $R^2$ and $R^3$, identical or different, are defined as above, and the group $R^7$ represents an alkylene or phenylene radical.

Among the groups $R^1$, $R^2$, $R^3$ and $R^4$, the following radicals will be mentioned: methyl, ethyl, propyl, isopropyl, primary butyl, secondary butyl, tert-butyl, butyl, amyl, phenyl or benzyl; the group $R^7$ can be a methylene, ethylene, propylene or phenylene group.

Preferably, the Q+ ammonium and phosphonium cations are selected from the group that is formed by N-butylpyridinium, N-ethylpyridinium, pyridinium, ethyl-3-methyl-1-imidazolium, butyl-3-methyl-1-imidazolium, hexyl-3-methyl-1-imidazolium, butyl-3-dimethyl-1,2-imidazolium, the (hydroxy-2-ethyl)-1-methyl-3-imidazolium cation, the (carboxy-2-ethyl)-1-methyl-3-imidazolium cation, diethylpyrazolium, N-butyl-N-methylpyrrolidinium, N-butyl-N-methylmorpholinium, trimethylphenylammonium, tetrabutylphosphonium, and tributyl-tetradecyl-phosphonium.

By way of example of $Q^+A^-$ salts that can be used according to the invention, it is possible to cite butyl-3-methyl-1-imidazolium bis(trifluoromethylsulfonyl)amide, butyl-3-dimethyl-1,2-imidazolium bis(trifluoromethylsulfonyl)amide, N-butyl-N-methylpyrrolidinium bis(trifluoromethylsulfonyl)amide, butyl-3-methyl-1-imidazolium tetrafluoroborate, butyl-3-dimethyl-1,2-imidazolium tetrafluoroborate, ethyl-3-methyl-1-imidazolium tetrafluoroborate, butyl-3-methyl-1-imidazolium hexafluoroantimonate, butyl-3-methyl-1-imidazolium trifluoroacetate, ethyl-3-methyl-1-imidazolium triflate, (hydroxy-2-ethyl)-1-methyl-3-imidazolium bis(trifluoromethylsulfonyl)amide, (carboxy-2-ethyl)-1-methyl-3-imidazolium bis(trifluoromethylsulfonyl)amide, N-butyl-N-methylmorpholinium bis(trifluoromethylsulfonyl)amide. These salts can be used by themselves or in a mixture.

Application in Catalysis

The suspension of metal nanoparticles in at least one non-aqueous ionic liquid that is thus defined is used, within the scope of the invention, as a catalytic composition in a process for hydrogenation of a non-aromatic unsaturated feedstock.

The Feedstock or Substrate

The feedstock or substrate that can be hydrogenated in the hydrogenation process according to the invention is a non-aromatic unsaturated feedstock and preferably a feedstock that comprises olefins, diolefins, and/or acetylenic compounds.

By way of examples, it is possible to cite the following olefinic, diolefinic and/or acetylenic compounds: ethylene, propylene, n-butene-1, the n-butenes-2, isobutene, pentenes, 1-2 propadiene, 1-2 and 1-3 butadiene, acetylene, propylene, vinyl and ethyl acetylenes, as well as other compounds whose boiling point is included in the interval of the "gasoline" fraction and that can be olefinic or diolefinic.

The compounds that are to be hydrogenated can be taken by themselves or in a mixture, pure or dilute, generally by at least one alkane, such that they are found in petroleum "fractions" that are obtained from the processes for refining petroleum that take place at high temperatures, such as, for example, steam-cracking, visbreaking, catalytic cracking and coking, which make possible a substantial production of unsaturated compounds whose formation is promoted at high temperatures.

The Hydrogenation Reaction

The hydrogenation reaction can be conducted in a closed system, in a half-open system, or continuously with one or more reaction stages. Vigorous stirring should ensure good contact between the reagent or reagents and the suspension of metal nanoparticles in the non-aqueous ionic liquid that acts as a catalytic composition.

The hydrogenation reaction can be conducted with a multiphase mixture (gas/liquid/liquid or gas/liquid). The suspension of metal nanoparticles in the non-aqueous ionic liquid can be separated from products by decanting and/or by extraction. It can be at least partially recycled and reused directly without intermediate treatment in the reaction phase. It is also possible to add fresh catalytic composition to remedy accidental losses or drops in performance levels.

The operating conditions of the hydrogenation reaction are as follows:

The reaction temperature is between 0° C. and 250° C., preferably between 20° C. and 150° C., and more preferably between 20 and 100° C. It is possible to operate above or below the melting point of the non-aqueous ionic liquid medium, whereby the dispersed solid state is not a limitation to the good course of the reaction.

The hydrogen pressure is between 0.1 and 20 MPa, preferably between atmospheric pressure and 5 MPa.

The molar ratio of substrate to metal is between 1 and 10,000, and preferably between 1 and 1,000.

One preferred embodiment of the process for hydrogenating a non-aromatic unsaturated feedstock according to the invention implements a suspension of metal nanoparticles in at least one non-aqueous ionic liquid that is selected from among butyl-1-methyl-3-imidazolium hexafluorophosphate [BMI][PF$_6$], butyl-1-methyl-3-imidazolium tetrafluoroborate [BMI][BF$_4$], and butyl-1-methyl-3-imidazolium bis-trifluoromethylsulfonyl amide [BMI][NTf$_2$], in which said metal nanoparticles comprise at least one transition metal in the zero-valence state, whereby the transition metal is selected from among rhodium and ruthenium, by themselves or in a mixture, and in which said metal nanoparticles are in contact with a nitrogen-containing ligand that is selected from among 2,2'-bipyridine and 2,4,6-tris-(2-pyridyl)-triazine or TPST.

EXAMPLES

The following examples illustrate the invention without limiting its scope:

Abbreviations that are Used:

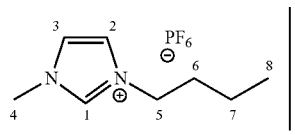

Butyl-1-methyl-3-imidazolium hexafluorophosphate [BMI][PF$_6$]

IL: Non-aqueous ionic liquid

Bpy: 2,2'-bipyridine

Example 1

Synthesis of Rh Nanoparticles in the Zero-Valence State Rh(O) by Chemical Reduction Using a Hydride as a Reducing Agent in the Ionic Liquid [BMI][PF$_6$]

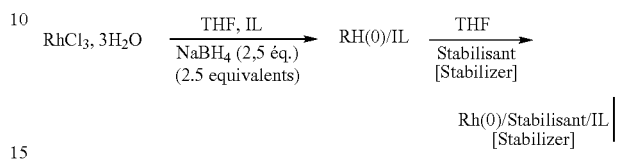

The suspension of metal nanoparticles of rhodium in the ionic liquid [BMI] [PF$_6$] is prepared at 20° C. 10 mg (3.8·10$^{-5}$ mol) of RhCl$_3$, 3H$_2$O is brought into solution in a mixture of THF (5 ml)/ionic liquid [BMI][PF$_6$] (2 ml). 3.6 mg (9.5·10$^{-5}$ mol; 2.5 equivalents) of NaBH$_4$ reducing agent, brought into solution in a minimum of water, is then added quickly to the mixture, while being stirred vigorously, at ambient temperature. Without waiting, 2.9 mg (1.9×10$^{-5}$ mol, 0.5 equivalent/metal) of 2,2'-bipyridine ligand, solubilized in 5 ml of tetrahydrofuran solvent or THF, (THF) is added to the reaction mixture while being stirred vigorously. The THF is then evaporated under reduced pressure, and the suspension of metal nanoparticles of rhodium is kept under vacuum and stirred vigorously for 2 hours.

The size distribution of the nanoparticles has a Gaussian form centered on 1.55 nm.

Example 2

Synthesis of Rhodium Nanoparticles in the Zero-Valence State Rh(O) by Chemical Reduction Using Molecular Hydrogen in the Ionic Liquid [BMI][PF$_6$]

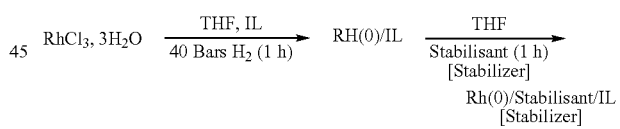

The suspension of metal nanoparticles of rhodium in the ionic liquid [BMI][PF$_6$] is prepared at 20° C. 10 mg (3.8·10$^{-5}$) of RhCl$_3$, 3H$_2$O is brought into solution in a mixture of THF (5 ml)/ionic liquid [BMI][PF$_6$] (2 ml). The entire unit is placed under vigorous stirring at ambient temperature and under 40 bar of molecular hydrogen H$_2$ in an autoclave. At the end of 1 hour, 2.9 mg (1.9×10$^{-5}$ mol, 0.5 equivalent/metal) of 2,2'-bipyridine ligand that is solubilized in 5 ml of THF solvent is added to the reaction mixture while being stirred vigorously. The reaction mixture is then placed again under vigorous stirring at ambient temperature and under 40 bar of H$_2$. At the end of 1 hour, the reaction is stopped, and the THF is evaporated under reduced pressure. The suspension of metal nanoparticles of rhodium that is obtained is then dried under vacuum, and vigorous stirring is maintained for 2 hours.

The size distribution of the nanoparticles has a Gaussian form that is centered on 2.33 nm.

Example 3

Synthesis of Ruthenium Nanoparticles in the Zero-Valence State Ru(0) by Chemical Reduction Using a Hydride as a Reducing Agent in the Ionic Liquid [BMI][PF$_6$]

The suspension of metal nanoparticles of ruthenium in the ionic liquid [BMI][PF$_6$] is prepared at 20° C. 7.9 mg ($3.8 \cdot 10^{-5}$ mol) of RuCl$_3$, 3H$_2$O is brought into solution in a mixture of THF (5 ml)/ionic liquid [BMI][PF$_6$] (2 ml). Then, 3.6 mg ($9.5 \cdot 10^{-5}$ mol; 2.5 equivalents) of reducing agent NaBH$_4$, brought into solution in a minimum of water, is added to the mixture quickly and while being stirred vigorously. Immediately afterward, 2.9 mg ($1.9 \times 10^{-5}$ mol, 0.5 equivalent/metal) of 2,2'-bipyridine ligand, solubilized in 5 ml of THF, is added quickly and while being stirred vigorously to the reaction mixture. The THF is then evaporated under reduced pressure, and the suspension of metal nanoparticles of ruthenium that is obtained is dried under vacuum and vigorous stirring is maintained for 2 hours.

The size of the nanoparticles is between 1.5 and 2.5 nm.

Example 4

General Procedure for Hydrogenation Under Pressure of Molecular Hydrogen 2 ml of a suspension of metal nanoparticles of rhodium in the ionic liquid [BMI][PF$_6$] that is prepared according to Example 1 and 100 equivalents/metal of substrate to be hydrogenated are introduced into a stainless steel autoclave that is equipped with a magnetic rod. The autoclave is then purged 4 times with hydrogen, the temperature is set at 80° C., and then the hydrogen pressure is set at 4 MPa. The reaction starts up with the beginning of the stirring. The progression of the reaction is tracked by gas phase chromatography (GPC). At the end of the reaction, the catalytic system is dispersed into 10 ml of acetonitrile CH$_3$CN, centrifuged for 10 minutes (15,300 rpm$^{-1}$; 20° C.). The sample is then analyzed by GPC.

Example 5

Procedure for Hydrogenation Under Atmospheric Pressure of Molecular Hydrogen The reactions under atmospheric pressure are carried out at 20° C. 2 ml of colloidal rhodium(O) suspension is introduced into a 25 ml glass flask. The desired quantity of substrate that is to be hydrogenated is added to the reaction mixture (in general, 100 equivalents/metal). The flask is then connected to a 500 ml gas burette. The assembly is filled with hydrogen after having purged the system under vacuum. The unit is placed under vigorous stirring (1,500 min$^{-1}$). The reaction is controlled by the volume of gas that is consumed and by gas phase chromatography. At the end of the reaction, the catalytic system is dispersed into 10 ml of CH$_3$CN, centrifuged for 10 minutes (15,300 rpm$^{-1}$; 20° C.). The sample is then analyzed by GPC. The results are grouped in Table 1 for different non-aromatic unsaturated substrates.

TABLE 1

Catalytic hydrogenation of non-aromatic unsaturated compounds under atmospheric pressure of hydrogen with Rh nanoparticles prepared according to Example 1

| Substrate | Product | Duration (Hours) | Conversion (%) |
|---|---|---|---|
| 1-Dodecene | Dodecane | 2 | 70 |
| 1-Tetradecene | Tetradecane | 2 | 60 |
| Cyclohexene | Cyclohexane | 2 | 77 |

Conditions: Catalyst: Rh(O), [BMI][PF$_6$] (2 ml), Bipyridine (0.5 equivalent/Rh), T = 20° C., 1 atmosphere of H$_2$, [Substrate]/[Metal] = 100 (mol)

Example 6

Hydrogenation of Cyclohexadiene

The suspension of metal nanoparticles of rhodium in the ionic liquid [BMI][PF$_6$] is produced as described in Example 1. The catalytic test is carried out as described in Example 5 but by using cyclohexadiene as a substrate to be hydrogenated. After 10 hours of reaction, the cyclohexadiene is completely hydrogenated by cyclohexane.

Example 7

Hydrogenation of Cyclohexene, Variation of the Ligand to Metal Ratio

The same operating method as in Example 6 is used, except that the substrate that is to be hydrogenated is cyclohexene, and except that the ratio between 2,2'-bipyridine and Rh is made to vary. The substrate to Rh molar ratio is 500. The results are grouped in Table 2.

TABLE 2

Effect of the 2,2'-Bipyridine/Rh Molar Ratio

| Equivalents of 2,2'-Bipyridine/Rh | Product | Conversion (% by Weight) |
|---|---|---|
| 0.5 | Cyclohexane | 50 |
| 1 | Cyclohexane | 17 |

Conditions: Catalyst: Rh(O)[BMI][PF$_6$] (2 ml), T = 20° C., 1 atmosphere of H$_2$, [Cyclohexene]/[Rh] = 500 mol, t = 5 hours

Example 8

Hydrogenation of Cyclohexene, Variation of the Nature of the Ionic Liquid

The same operating method as in Example 7 is used, except that the temperature is set at 40° C., and except that the nature of the ionic liquid is made to vary. The molar ratio of substrate to Rh is 500. The results are grouped in Table 3.

TABLE 3

Effect of the Nature of the Ionic Liquid

| Ionic Liquid | Product | Conversion (% by Weight) |
|---|---|---|
| [BMI][NTf$_2$] | Cyclohexane | 50 |
| [BMI][BF$_4$] | Cyclohexane | 65 |

Conditions: Catalyst: Rh(O) IL (2 ml), 2,2'-Bipyridine (0.5 equivalent), T = 40° C., 1 atmosphere of H$_2$, [Cyclohexene]/[Rh] = 500 mol, t = 5 hours, NTf$_2$ = bistrifluoromethylsulfonyl amide

The invention claimed is:

1. A suspension of metal nanoparticles with a mean size of between 1 and 20 nanometers, in at least one non-aqueous ionic liquid, wherein said suspension also contains at least one nitrogen-containing ligand, in which said metal nanoparticles comprise at least one transition metal in a zero valence state selected from among rhodium, ruthenium, iridium, nickel, and platinum by themselves or in a mixture and in which said nitrogen-containing ligand is selected from the group that is formed by linear compounds that comprise at least one nitrogen atom, non-aromatic cyclic compounds comprising at least one nitrogen atom, non-condensed aromatic compounds comprising at least one nitrogen atom, condensed aromatic compounds comprising at least one group of two aromatic cycles that are condensed two by two, and at least one nitrogen atom, condensed aromatic compounds comprising at least 3 aromatic cycles and 1 nitrogen atom, and condensed aromatic compounds comprising at least 3 aromatic cycles and at least 2 nitrogen atoms that are located in the same aromatic cycle, and the molar ratio between said at least one nitrogen-containing ligand and said transition metal is strictly less than 1.

2. A suspension of metal nanoparticles according to claim 1, in which said transition metal is selected from among rhodium, ruthenium and iridium, by themselves or in a mixture.

3. A suspension of metal nanoparticles according to claim 2, in which said transition metal is rhodium.

4. A suspension of metal nanoparticles according to claim 2, in which said transition metal is ruthenium.

5. A suspension of metal nanoparticles according to claim 1, in which said nitrogen-containing ligand is selected from the group that is formed by linear compounds that comprise at least one nitrogen atom from any of: alkylamines, diamines, and polyamines and polyethyleneimines.

6. A suspension of metal nanoparticles according to claim 1, in which said nitrogen-containing ligand is selected from the group that is formed by the non-aromatic cyclic compounds that comprise at least one nitrogen atom from any of: bipiperidines and substituted bipiperidines, polyazacycloalkanes, oxazolidines and substituted oxazolidines, oxazolines and substituted oxazolines.

7. A suspension of metal nanoparticles according to claim 1, in which said nitrogen-containing ligand is selected from the group that is formed by the non-condensed aromatic compounds that comprise at least one nitrogen atom from any of: pyridines and substituted pyridines, bipyridines and substituted bipyridines, bis(2-pyridyl)alkanes, bis(3-pyridyl)alkanes, bis(4-pyridyl)alkanes and bis(2-pyridinyl)alkanes, and substituted bis(2-pyridyl)alkanes, substituted bis(3-pyridyl)alkanes, substituted bis(4-pyridyl)alkanes and substituted bis(2-pyridinyl)alkanes, pyrazines and substituted pyrazines, and triazines and substituted triazines.

8. A suspension of metal nanoparticles according to claim 7, in which said nitrogen-containing ligand is tetra-2-pyridinyl-pyrazine or bis-pyridyl-pyrazine.

9. A suspension of metal nanoparticles according to claim 7, in which said nitrogen-containing ligand is 2,4,6-tris-(2-pyridyl)-triazine.

10. A suspension of metal nanoparticles according to claim 1, in which said nitrogen-containing ligand is selected from the group that is formed by the condensed aromatic compounds that comprise at least one group of two aromatic cycles that are condensed two by two and at least one nitrogen atom from any of: naphpyridines and substituted naphpyridines, quinolines and substituted quinolines, biquinolines and substituted biquinolines, and isoquinolines and substituted isoquinolines.

11. A suspension of metal nanoparticles according to claim 1, in which said nitrogen-containing ligand is selected from the group that is formed by the condensed aromatic compounds that comprise at least 3 aromatic cycles and 1 nitrogen atom, any of: dibenzopyridines and substituted dibenzopyridines, and phenanthridines and substituted phenanthridines.

12. A suspension of metal nanoparticles according to claim 1, in which said nitrogen-containing ligand is selected from the group that is formed by the condensed aromatic compounds that comprise at least 3 aromatic cycles and at least two nitrogen atoms that are located on the same aromatic cycle, including a ligand from any of: phenazines and substituted phenazines.

13. A suspension of metal nanoparticles according to claim 1, in which said at least one non-aqueous ionic liquid is a compound that is represented by the general formula $Q^+A^-$ in which the $A^-$ anions are selected from among the following anions: halides, nitrates, sulfates, alkylsulfates, phosphates, alkylphosphates, acetates, haloacetates, tetrafluoroborates, tetrachloroborates, hexafluorophosphates, trifluoro-tris-(pentafluoroethyl)phosphates, hexafluoroantimonates, fluorosulfonates, alkylsulfonates, perfluoroalkylsulfonates, bis(perfluoroalkylsulfonyl)amides, arenesulfonates, optionally substituted by halogen or haloalkyl groups, tetraphenylborate and the tetraphenylborate anions whose aromatic cores are substituted, the tetra-(trifluoroacetoxy)-borate anion, the bis-(oxalato)-borate anion, the dicyanamide anion, the tricyanomethylide anion, as well as the chloroaluminate anions or the chlorozincate anions, and the chloroferrate anions, and in which the $Q^+$ cations are selected from among the group that is formed by phosphoniums, ammoniums, guanidiniums and sulfoniums.

14. A suspension of metal nanoparticles according to claim 1 in at least one non-aqueous ionic liquid that is selected from among butyl-1-methyl-3-imidazolium hexafluorophosphate, butyl-1-methyl-3-imidazolium tetrafluoroborate, and butyl-1-methyl-3-imidazolium bis-trifluoromethylsulfonyl amide, in which said metal nanoparticles comprise at least one transition metal in the zero-valence state, whereby the transition metal is selected from among rhodium and ruthenium, by themselves or in a mixture, and in which said metal nanoparticles are in contact with a nitrogen-containing ligand that is selected from among 2,2'-bipyridine and 2,4,6-tris-(2-pyridyl)-triazine.

15. A suspension of metal nanoparticles according to claim 1, in which the molar ratio between said ligand and said metal of the metallic precursor is between 0.05 and 0.6.

16. A process for preparation of the suspension of metal nanoparticles according claim 1, in which a metal precursor, said non-aqueous ionic liquid, said nitrogen-containing ligand and a reducing agent are brought into contact, said contact being followed by stirring and the addition of different components that can be done in any order.

17. A process for preparation of the suspension of metal nanoparticles according to claim 16, in which said nitrogen-containing ligand is added in a second stage following a first stage of bringing into contact said metal precursor, said non-aqueous ionic liquid, and said reducing agent.

18. A process for preparation of the suspension of metal nanoparticles according to claim 16, in which the operation is carried out in the presence of an organic solvent that is selected from among aromatic hydrocarbons, non-aromatic hydrocarbon compounds, halogenated hydrocarbon compounds, ethers, and alcohols.

19. A process for preparation of the suspension of metal nanoparticles according to claim 16, in which the metal precursors are metallic salts of the transition metals that are selected from among halides, acetates, sulfates, carboxylates, phenates and acetylacetonates.

20. A process for preparation of the suspension of metal nanoparticles according to claim 16, in which the metal precursors are organometallic complexes or oxides.

21. A process for preparation of the suspension of metal nanoparticles according to claim 16, in which the reducing agent is selected from among the metals and the metallic salts, the hydrides, the organic compounds and the organic solvents that can be oxidized.

22. A process for preparation of the suspension of metal nanoparticles according to claim 21, in which the reducing agent is a metal that is selected from among zinc, aluminum, and lithium.

23. A process for preparation of the suspension of metal nanoparticles according to claim 21, in which the reducing agent is a hydride that is selected from among sodium borohydride, potassium borohydride, or lithium aluminum tetrahydride.

24. A process for preparation of the suspension of metal nanoparticles according to claim 21, in which the reducing agent is an organic compound that is selected from among ascorbic acid and hydrazine.

25. A process comprising conducting hydrogenation of a substrate comprising non-aromatic unsaturated feedstock under hydrogenation conditions in contact with a catalytic composition comprising a suspension of metal nanoparticles in a non-aqueous ionic liquid according to claim 1.

26. A process for hydrogenation according to claim 25, in which the hydrogenation temperature is between 0° C. and 250° C., under a hydrogen pressure of between 0.1 and 20 MPa, and with a molar ratio of said substrate to metal nanoparticles of between 1 and 10,000.

27. A process for hydrogenation according to claim 25, in which the feedstock comprises—olefins, diolefins and/or acetylenic compounds.

28. A process according to claim 26, wherein the molar ratio is between 1 and 1,000.

29. A process according to claim 25, wherein the suspension of metal nanoparticles was produced in an organic solvent and further comprising removing the organic solvent from the suspension of metal nanoparticles prior to conducting the hydrogenation.

* * * * *

UNITED STATES PATENT AND TRADEMARK OFFICE
CERTIFICATE OF CORRECTION

PATENT NO.       : 8,395,003 B2
APPLICATION NO.  : 12/597341
DATED            : March 12, 2013
INVENTOR(S)      : Leger et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 574 days.

Signed and Sealed this
First Day of September, 2015

Michelle K. Lee
*Director of the United States Patent and Trademark Office*